United States Patent

Pak et al.

Patent Number: 5,707,931
Date of Patent: Jan. 13, 1998

[54] 4-AMINO-2-QUINOLINONE DERIVATIVES

[75] Inventors: Chwang Siek Pak; Eun Bok Choi; Gyu Hwan Yon; Heui Cheol Yang; Hyeon Kyu Lee; Ge Hyeong Lee; Jin Pyo Lee; Gyung Ja Choi, all of Daejeon, Rep. of Korea

[73] Assignee: Korea Research Intsituted of Chemical Technology, Rep. of Korea

[21] Appl. No.: 564,238

[22] PCT Filed: Jun. 21, 1994

[86] PCT No.: PCT/KR94/00079

§ 371 Date: Dec. 19, 1995

§ 102(e) Date: Dec. 19, 1995

[87] PCT Pub. No.: WO95/00488

PCT Pub. Date: Jan. 5, 1995

[30] Foreign Application Priority Data

Jun. 22, 1993 [KR] Rep. of Korea .................. 93-11382

[51] Int. Cl.⁶ .................. A61K 31/47; C07D 215/30
[52] U.S. Cl. .................. 504/247; 546/156
[58] Field of Search .................. 546/656; 504/247

[56] References Cited

FOREIGN PATENT DOCUMENTS

92/1745  10/1992  WIPO .

*Primary Examiner*—C. Warren Ivy
*Assistant Examiner*—D. Margaret M. Mach
*Attorney, Agent, or Firm*—Finnegan, Henderson, Farabow, Garrett & Dunner L.L.P.

[57] ABSTRACT

The present invention relates to novel 4-amino-2-quinolinone derivatives of the formula (I) useful in agriculture, especially as fungicides, insecticides and herbicides

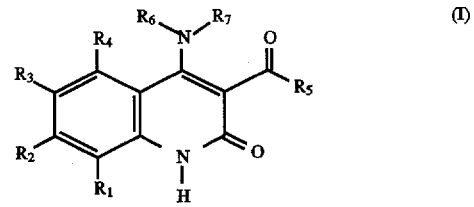

wherein, $R_1$, $R_2$, $R_3$ and $R_4$ are independently hydrogen, halogen, $C_1$–$C_{10}$ alkyl, $C_1$–$C_3$ haloalkyl, $C_1$–$C_8$ alkoxy, $C_1$–$C_3$ haloalkoxy, $C_1$–$C_3$ alkylthio, $C_1$–$C_3$ haloalkyithio, $NO_2$, CN, $C_1$–$C_4$ alkoxy carbonyl, phenyl, phenoxy, benzoyl, benzenesulfonyl, benzyl or morpholine; $R_5$ is hydrogen, $C_1$–$C_6$ alkyl, cyclopropyl, phenyl, halophenyl, benzyl or phenylthiomethyl; $R_6$ is hydrogen, $C_1$–$C_5$ alkyl, $C_3$–$C_6$ alkenyl or $C_3$–$C_6$ alkynyl; and $R_7$ is

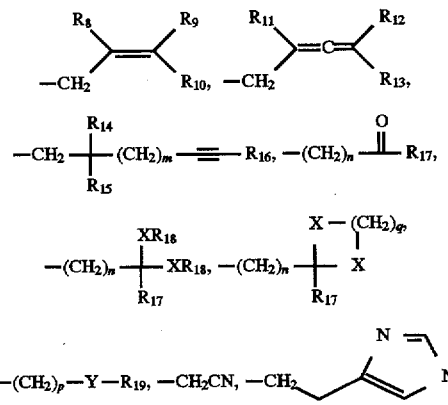

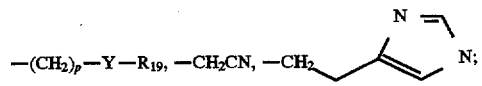

wherein, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, X, Y, m, n, p and q are defined within the description.

5 Claims, No Drawings

4-AMINO-2-QUINOLINONE DERIVATIVES

This is the U.S. national stage application of PCT/KR94/00079 filed Jun. 21, 1994, published as WO/95/00488 on Jan. 5, 1995.

BACKGROUND OF THE INVENTION

Field of the Invention

The present invention relates to novel 4-amino-2-quinolinone derivatives of the following formula (I) useful as fungicides, insecticides and herbicides.

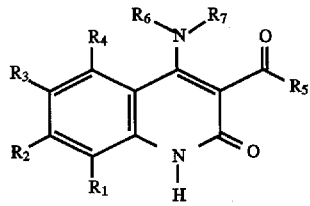

wherein, $R_1$, $R_2$, $R_3$ and $R_4$ are independently hydrogen, halogen, $C_1$–$C_{10}$ alkyl, $C_1$–$C_3$ haloalkyl, $C_1$–$C_8$ alkoxy, $C_1$–$C_3$ haloalkoxy, $C_1$–$C_3$ alkylthio, $C_1$–$C_3$ haloalkylthio, $NO_2$, CN, $C_1$–$C_4$ alkoxy carbonyl, phenyl, phenoxy, benzoyl, benzenesulfonyl, benzyl or morpholine;

$R_5$ is $C_1$–$C_6$ alkyl, cyclopropyl, phenyl, halophenyl, benzyl or phenylthiomethyl;

$R_6$ is selected from hydrogen, $C_1$–$C_5$ alkyl, $C_3$–$C_6$ alkenyl and $C_3$–$C_6$ alkynyl group;

$R_7$ is

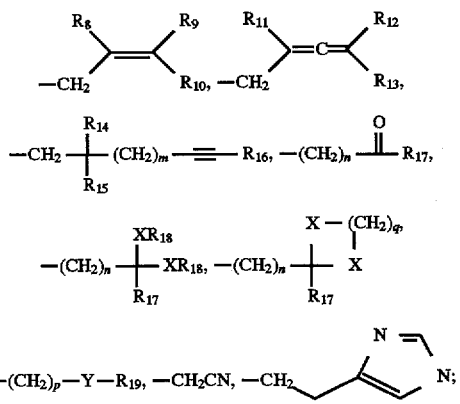

wherein, $R_8$, $R_9$, $R_{10}$, $R_{11}$, $R_{12}$, $R_{13}$, $R_{14}$, $R_{15}$, $R_{16}$ is hydrogen, halogen, $C_1$–$C_6$ alkyl, alkoxyalkyl, halophenyl, phenyl or $(R_{20})_3Si$ and $R_8$, $R_9$, $R_{10}$ are not hydrogen at the same time;

$R_{17}$ is hydrogen or $C_1$–$C_5$ alkyl;

$R_{18}$, $R_{19}$ is $C_1$–$C_5$ alkyl;

X is oxygen or sulfur;

Y is sulfur or —S(=O)—;

$R_{20}$ is $C_1$–$C_5$ alkyl;

m, n, p, q is 0 to 4.

Description of the Related Art

Prior to this invention, one report on the synthesis of 3-acetyl-4-dimethylamino-2-quinolinone from phenylisocynate and 1-dimethylamino-3-oxo-1-butylene by [4+2] cycloaddition reaction (Helv. Chim. Acta., 1969, 52, 2641.) was disclosed but no attempt for the evaluation of biological activity of the related compounds was reported.

According to the known methods, it is difficult to introduce various substituents to aromatic ring, 4-amino group, and 3-acyl group of 2-quinolinone skeleton.

Especially, synthesis of 4-monosubstituted amino-2-quinolinones which are core of the present invention is impossible to be produced by known methods.

In the present invention, variety of new 4-amino-2-quinolinone derivatives having various substituents were synthesized conveniently from various amines and 4-sulfinyl-2-quinolinones of which synthesis was previously disclosed by present inventors (Korea Patent No.70672).

Moreover new 4-amino-2-quinolinone derivatives of the present invention showed powerful fungicidal activity as well as insecticidal and herbicidal activity.

Therefore, the present invention contains development of novel 4-amino-2-quinolinone derivatives that have superior fungicide, insecticide and herbicide activities and their preparation for use.

SUMMARY OF THE INVENTION

The objective of the present invention is to provide novel 4-amino-2-quinolinone derivatives of formula (I) which have fungicidal, insecticidal and herbicidal activity and their preparation processes.

Another objective is to provide agricultural preparation containing a compound of formula (I) as active ingredient.

DETAILED DESCRIPTION OF THE INVENTION

The present invention relates to 4-amino-2-quinolinone compounds of the formula (I) and agricultural preparations containing compounds of the formula (I) as active ingredient.

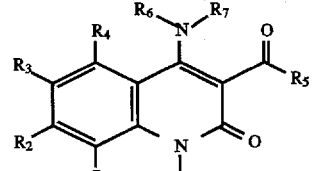

wherein, $R_1$, $R_2$, $R_3$, $R_4$, $R_5$, $R_6$ and $R_7$ are respectively defined as described previously.

In this invention, 4-amino-2-quinolinone compounds of the formula (I) were prepared by reacting 4-sulfinyl-2-quinolinone of formula (II) with the amines ($HNR_6R_7$) of the formula (III) in presence of inert solvent.

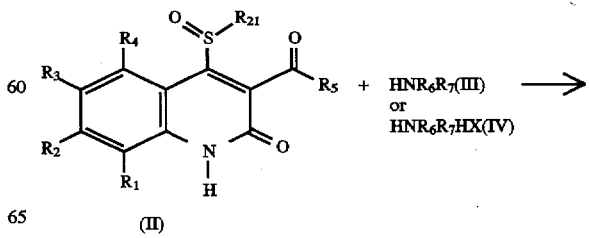

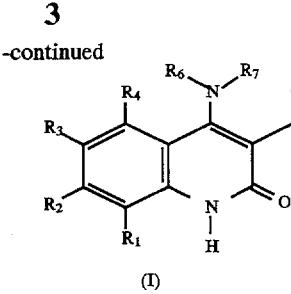

(I)

wherein, $R_1$, $R_2$, $R_3$, $R_4$, $R_5$, $R_6$ and $R_7$ are defined as previously and $R_{21}$ is $C_1$–$C_3$ alkyl.

When the amine compound of formula (III) is in salt form, such as primary or secondary ammonium hydrochlorides ($HNR_6R_7$—HCl), sulfates, carbonates, oxalates or tosylates, 1~2 equivalents of an acid remover, for example, trialkylamines (such as triethylamine) or inorganic base (such as sodium hydroxide, potassium carbonate), may be used.

The inert solvents used in the present invention may be, for example, ethers such as diethylether, diisopropyl ether, tetrahydrofuran, dioxane, diphenylether, etc.; hydrocarbons such as benzene, toluene, xylene, ligroine, etc.; hydrocarbon halides such as dichloroethane, chloroform, carbon tetrachloride, etc.; esters such as ethyl acetate, ethyl propionate, etc.; chlorobenzenes such as monochlorobenzene, dichlorobenzene, etc.; aprotic polar solvents such as N,N-dimethylformamide, dimethyl sulfoxide, etc. The above reaction can be carried out in the absence of solvent but for effective reaction use of proper solvent is recommended and pyridine and trialkylamine may be used for two purposes of base or a solvent.

The reaction can be carried out at 0°~260° C., preferably between room temperature and boiling point of the solvent, and then the reaction time is preferably of 0.5~8 hr.

As a result of the reaction, when the free amine compound ($HNR_6R_7$) of formula (III) is used, the crude product is obtained by evaporating the solvent under the reduced pressure.

But, when the salt form of amine compound of formula (III) is used, the crude product may be obtained by following process; the solvent is evaporated under the reduced pressure; water is added to dissolve the salts; the resulting mixture is extracted with water-immiscible organic solvents such as methylenechloride, chloroform, ethyl acetate, etc.; and the organic layer is evaporated under the reduced pressure to afford the crude product.

Compounds (Ib) shown below can be obtained by acid hydrolysis of compounds (Ia), a kind of 4-amino-2-quinolinone derivatives of formula (I)

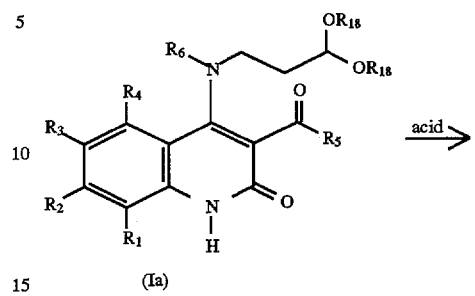

(Ia)

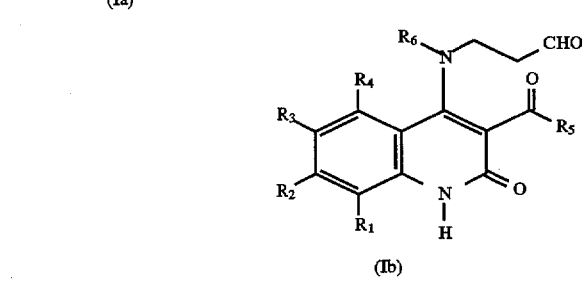

(Ib)

wherein, $R_1$, $R_2$, $R_3$, $R_4$, $R_5$, $R_6$ and $R_{18}$ are defined as previously.

The hydrolysis reaction of compounds (Ia) to compounds (Ib) can be done in the presence of mineral acids such as hydrochloric acid, sulfuric acid, etc. or organic acids such as acetic acid, propionic acid, etc. and the reaction could be carried from room temperature to the boiling point of the solvent.

The 4-amino-2-quinolinone derivatives of formula (I) described above may be purified by column chromatography or recrystallized from the following solvents; alcohol solvents such as methanol, ethanol, etc.; esters of organic acid such as ethyl acetate, methyl acetate, etc.; hydrocarbon solvents such as pentane, hexane, etc.; ethers such as ethylether, tetrahydrofuran, etc.

New compounds of 4-amino-2-quinolinone (I) prepared by present invention are typically listed in following Table (I).

TABLE 1

4-Amino-2-quinolinone derivatives

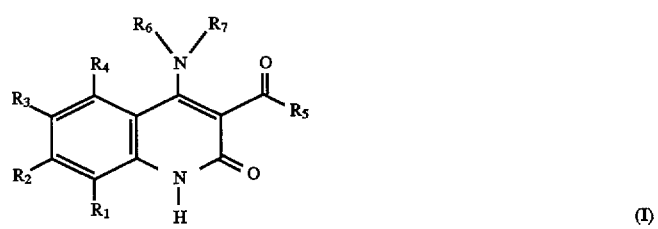

(I)

| No. | $R_1$ | $R_2$ | $R_3$ | $R_4$ | $R_5$ | $R_6$ | $R_7$ | m.p. (°C.) |
|-----|-------|-------|-------|-------|-------|-------|-------|------------|
| 1 | $CF_3$ | H | H | H | Me | $H_2C$—\\ | $H_2C$—\\ | 36–38 |
| 2 | Cl | Cl | H | H | Me | $H_2C$—\\ | $H_2C$—\\ | 48–50 |

TABLE 1-continued

4-Amino-2-quinolinone derivatives

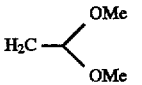

(I)

| No. | $R_1$ | $R_2$ | $R_3$ | $R_4$ | $R_5$ | $R_6$ | $R_7$ | m.p. (°C.) |
|---|---|---|---|---|---|---|---|---|
| 3 | Cl | H | H | $CF_3$ | Me | $H_2C-CH=CH_2$ | $H_2C-CH=CH_2$ | 75–77 |
| 4 | Me | F | H | H | Me | $H_2C-CH=CH_2$ | $H_2C-CH=CH_2$ | 61–64 |
| 5 | CN | H | H | H | Me | $H_2C-CH=CH_2$ | $H_2C-CH=CH_2$ | 70–71 |
| 6 | Cl | H | H | Cl | Me | $H_2C-CH=CH_2$ | $H_2C-CH=CH_2$ | 76–78 |
| 7 | $CF_3$ | H | Cl | H | c-Pr | $H_2C-CH=CH_2$ | $H_2C-CH=CH_2$ | 104–107 |
| 8 | $CF_3$ | H | Cl | H | i-Pr | $H_2C-CH=CH_2$ | $H_2C-CH=CH_2$ | 83–85 |
| 9 | $CF_3$ | H | Cl | H | c-Pr | H | $H_2C-CH(OMe)_2$ | 191–193 |
| 10 | $CF_3$ | H | Cl | H | i-Pr | H | $H_2C-CH(OMe)_2$ | 159–161 |
| 11 | $CF_3$ | H | Cl | H | Et | H | $H_2C-CH(OMe)_2$ | 171–172 |
| 12 | $CF_3$ | H | Cl | H | Me | Me | $H_2C-C\equiv CH$ | 86–87 |
| 13 | $CF_3$ | H | Cl | H | i-Pr | Me | $H_2C-C\equiv CH$ | 99–101 |
| 14 | $CF_3$ | H | Cl | H | c-Pr | Me | $H_2C-C\equiv CH$ | 118–120 |
| 15 | $CF_3$ | H | H | H | Me | Me | $H_2C-C\equiv CH$ | 64–69 |
| 16 | $CF_3$ | H | Cl | H | Et | Me | $H_2C-C\equiv CH$ | 70–72 |
| 17 | Cl | Cl | H | H | Me | Me | $H_2C-C\equiv CH$ | 110–112 |
| 18 | Cl | Cl | H | H | Me | H | $H_2C-CH(OMe)_2$ | 210–211 |
| 19 | $CF_3$ | F | H | H | Me | H | $H_2C-CH(OMe)_2$ | 161–162 |
| 20 | Cl | H | H | $NO_2$ | Me | H | $H_2C-CH(OMe)_2$ | 213–214 |

TABLE 1-continued

4-Amino-2-quinolinone derivatives (I)

| No. | $R_1$ | $R_2$ | $R_3$ | $R_4$ | $R_5$ | $R_6$ | $R_7$ | m.p. (°C.) |
|---|---|---|---|---|---|---|---|---|
| 21 | $CF_3$ | H | Cl | H | c-Pr | H | $H_2C-\equiv$ | 179–181 |
| 22 | $CF_3$ | H | Cl | H | Et | H | $H_2C-\equiv$ | 185–186 |
| 23 | H | H | n-$C_6H_{13}$ | H | Me | H | $H_2C-\equiv$ | 129–132 |
| 24 | $CF_3$ | H | Cl | H | Me | H | $H_2C-\equiv$ | 210–212 |
| 25 | Me | H | H | H | Me | H | $H_2C-\equiv$ | 232–234 |
| 26 | Cl | H | H | $NO_2$ | H | H | $H_2C-\equiv$ | 217–219 |
| 27 | Cl | Cl | H | H | Me | H | $H_2C-\equiv$ | 245–249 |
| 28 | $CF_3$ | H | Cl | H | i-Pr | H | $H_2C-\equiv$ | 166–168 |
| 29 | $CF_3$ | H | Cl | H | Me | H | $H_2C-CH=CH_2$ | 213–215 |
| 30 | $CF_3$ | H | Cl | H | i-Pr | H | $H_2C-\equiv$ | 167–169 |
| 31 | $CF_3$ | H | Cl | H | i-Pr | H | $H_2C-CH(OEt)_2$ | 55–56 |
| 32 | $CF_3$ | H | Cl | H | i-Pr | H | $H_2C-CH_2CHO$ | 53–54 |
| 33 | $CF_3$ | H | Cl | H | i-Pr | H | $H_2C-CH=CHCl$ | E & Z |
| 34 | $CF_3$ | H | Cl | H | i-Pr | H | $H_2C-\equiv-SiMe_3$ | 177–178 |
| 35 | $CF_3$ | H | Cl | H | c-Pr | H | $H_2C-\equiv$ | 183–184 |
| 36 | $CF_3$ | H | Cl | H | Me | H | $H_2C-CN$ | 218–220 |
| 37 | $CF_3$ | H | Cl | H | i-Pr | H | $H_2C-C(OCH_2CH_2O)$ | 129–130 |
| 38 | $CF_3$ | H | Cl | H | i-Pr | H | $H_2C-\equiv$ | 114–116 |
| 39 | $CF_3$ | H | Cl | H | Me | H | $H_2C-C(OCH_2CH_2O)$ | 168–169 |
| 40 | $CF_3$ | H | Cl | H | c-Pr | H | $H_2C-\equiv-SiMe_2Bu-t$ | 191–193 |

TABLE 1-continued

4-Amino-2-quinolinone derivatives $$(I)$$

| No. | $R_1$ | $R_2$ | $R_3$ | $R_4$ | $R_5$ | $R_6$ | $R_7$ | m.p. (°C.) |
|---|---|---|---|---|---|---|---|---|
| 41 | $CF_3$ | H | Cl | H | c-Pr | H | $H_2C-\equiv-SiMe_3$ | 181–182 |
| 42 | $CF_3$ | H | Cl | H | Me | H | $H_2C-\equiv-SiMe_3$ | 172–173 |
| 43 | $CF_3$ | H | Cl | H | Me | H | $H_2C-\equiv-SiMe_2Bu\text{-}t$ | 191–192 |
| 44 | CF | H | Cl | H | Et | H | $H_2C-\equiv$ | 183–184 |
| 45 | $CF_3$ | H | Cl | H | Me | H | $H_2C\text{-CH(OEt)}_2$ | 104–105 |
| 46 | $CF_3$ | H | Cl | H | Me | H | $H_2C\text{-CH}_2\text{-}C\equiv$ | 132–133 |
| 47 | $CF_3$ | H | Cl | H | Me | H | $H_2C-\equiv$ | 240–241 |
| 48 | $CF_3$ | H | Cl | H | i-Pr | H | $H_2C-\equiv-SiMe_2Bu\text{-}t$ | 185–186 |
| 49 | $CF_3$ | H | Cl | H | Et | H | $H_2C-\equiv-SiMe_3$ | 154–155 |
| 50 | $CF_3$ | H | Cl | H | Et | H | $H_2C-\equiv-SiMe_2Bu\text{-}t$ | 153–154 |
| 51 | $CF_3$ | H | Cl | H | Me | H | $Me_2C(-\equiv)$ | 172–173 |
| 52 | $CF_3$ | H | Cl | H | Me | H | $H_2C\text{-CH}_2\text{-CHO}$ | 156–157 |
| 53 | $CF_3$ | H | Cl | H | Et | H | $H_2C-\equiv$ | 183–184 |
| 54 | $CF_3$ | H | Cl | H | Et | H | $H_2C\text{-CH}_2\text{-}C\equiv$ | 124–126 |
| 55 | $CF_3$ | H | Cl | H | Et | H | $H_2C\text{-}C(\text{O-CH}_2\text{-CH}_2\text{-O})$ | 188–189 |
| 56 | $CF_3$ | H | Cl | H | c-Pr | H | $H_2C-\equiv$ | 196–197 |
| 57 | $CF_3$ | H | Cl | H | c-Pr | H | $H_2C\text{-CH}_2\text{-}C\equiv$ | 134–135 |
| 58 | $CF_3$ | H | Cl | H | c-Pr | H | $H_2C\text{-}C(\text{O-CH}_2\text{-CH}_2\text{-O})$ | 181–182 |
| 59 | $CF_3$ | H | Cl | H | c-Pr | H | $H_2C\text{-CH}_2\text{-CH(OEt)}_2$ | 111–112 |

TABLE 1-continued

4-Amino-2-quinolinone derivatives

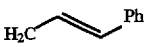

(I)

| No. | $R_1$ | $R_2$ | $R_3$ | $R_4$ | $R_5$ | $R_6$ | $R_7$ | m.p. (°C.) |
|---|---|---|---|---|---|---|---|---|
| 60 | $CF_3$ | H | Cl | H | Et | H | 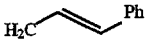 | 181–182 |
| 61 | $CF_3$ | H | Cl | H | c-Pr | H | 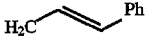 | 152–153 |
| 62 | $CF_3$ | H | Cl | H | Me | H | 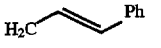 | 170–172 |
| 63 | $CF_3$ | H | Cl | H | c-Pr | H | 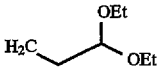 | 185–186 |
| 64 | $CF_3$ | H | Cl | H | Et | H | 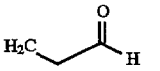 | 87–88 |
| 65 | $CF_3$ | H | Cl | H | Et | H | 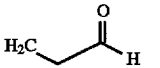 | 91–94 |
| 66 | $CF_3$ | H | Cl | H | c-Pr | H | 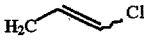 | 127–130 |
| 67 | $CF_3$ | H | Cl | H | Me | H | 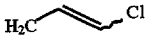 | E & Z |
| 68 | $CF_3$ | H | Cl | H | Et | H |  | E & Z |
| 69 | —CHCH=CHCH— | | Cl | H | c-Pr | H | $H_2C\!\!=\!\!\!\equiv$ | 222 (dec.) |
| 70 | $CF_3$ | H | H | H | Me | H | $H_2C\!\!=\!\!\!\equiv$ | 192–194 |
| 71 | Cl | H | H | H | Et | H | $H_2C\!\!=\!\!\!\equiv$ | 212–214 |
| 72 | $CF_3$ | H | Cl | H | c-Pr | H |  | 136–137 |
| 73 | $CF_3$ | H | Cl | H | c-Pr | $H_2C\!\!=\!\!\!\equiv$ | $H_2C\!\!=\!\!\!\equiv$ | 140–142 |
| 74 | $CF_3$ | H | Cl | H | i-Bu | H | $H_2C\!\!=\!\!\!\equiv$ | 179–180 |
| 75 | $CF_3$ | H | Cl | H | Me | H |  | 136–137 |
| 76 | $CF_3$ | H | Cl | H | Et | H | 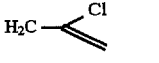 | 149–150 |
| 77 | $CF_3$ | H | Cl | H | i-Pr | H |  | 135–136 |
| 78 | $CF_3$ | H | Cl | H | c-Pr | H |  | E & Z |
| 79 | H | H | Cl | H | Me | H | $H_2C\!\!=\!\!\!\equiv$ | 166–168 |

TABLE 1-continued

4-Amino-2-quinolinone derivatives

| No. | R₁ | R₂ | R₃ | R₄ | R₅ | R₆ | R₇ | m.p. (°C.) |
|-----|-----|-----|-----|-----|-----|-----|-----|------------|
| 80 | F | H | H | H | H | H | H₂C—≡ | 206–208 |
| 81 | Me | H | H | H | Me | H | H₂C—≡ | 229–231 |
| 82 | CF₃ | H | Cl | H | c-Pr | H | H₂C—≡—Ph | 227–228 |
| 83 | CF₃ | H | Cl | H | Et | H | H₂C—≡—Ph | 191–193 |
| 84 | CF₃ | H | Cl | H | i-Pr | H | H₂C—≡—Ph | 166–167 |
| 85 | CF₃ | H | Cl | H | Et | H₂C—≡ | H₂C—≡ | 91–94 |
| 86 | CF₃ | H | Cl | H | Me | H₂C—≡ | H₂C—≡ | 115–117 |
| 87 | CF₃ | H | Cl | H | i-Pr | H | H₂C—≡ | — |
| 88 | H | —OCH₂CH₂O— | | H | c-Pr | H | H₂C—≡ | 230 (dec.) |
| 89 | CF₃ | H | Cl | H | i-pr | H | H₂C—CH(OEt)₂ | 113–114 |
| 90 | CF₃ | H | Cl | H | i-Pr | H | 2,2-dimethyl-1,3-dioxolan-4-ylmethyl | 154–155 |
| 91 | CF₃ | H | Cl | H | i-Pr | H | H₂C—≡ | 196–197 |
| 92 | CF₃ | H | Cl | H | i-Bu | H | H₂C—C≡ | 128–130 |
| 93 | CF₃ | H | Cl | H | i-Pr | H₂C—≡ | H₂C—≡ | 93–94 |
| 94 | CF₃ | H | H | H | Me | H₂C—≡ | H₂C—≡ | 94–95 |
| 95 | CF₃ | H | Cl | H | Et | H | 1,3-dioxan-2-ylmethyl | 159–161 |
| 96 | CF₃ | H | Cl | H | i-Bu | H | 1,3-dioxan-2-ylmethyl | 174–175 |
| 97 | CF₃ | H | Cl | H | i-Pr | H | 1,3-dioxan-2-ylmethyl | 140–142 |

TABLE 1-continued
4-Amino-2-quinolinone derivatives
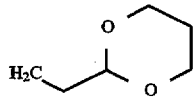
(I)
| No. | R₁ | R₂ | R₃ | R₄ | R₅ | R₆ | R₇ | m.p. (°C.) |
|---|---|---|---|---|---|---|---|---|
| 98 | CF₃ | H | Cl | H | c-Pr | H | 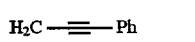 | 166–168 |
| 99 | CF₃ | H | Cl | H | Me | H | H₂C≡≡—Ph | 200–201 |
| 100 | CF₃ | H | Cl | H | c-Pr | H | H₂C≡≡—OMe | — |
| 101 | CF₃ | H | Cl | H | PhCH₂ | H | H₂C≡≡ | 154–156 |
| 102 | CF₃ | H | Cl | H | Me | H | H₂C—SMe | 146–147 |
| 103 | CF₃ | H | Cl | H | Me | H | Ph | 125–127 |
| 104 | CF₃ | H | Cl | H | i-Bu | H | 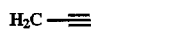Ph | 100–102 |
| 105 | CF₃ | H | Cl | H | c-Pr | H | Ph | 122–126 |
| 106 | CF₃ | H | Cl | H | Et | H | Ph | 107–109 |
| 107 | CF₃ | H | Cl | H | c-Pr | H |  | 185–186 |
| 108 | CF₃ | H | Cl | H | i-Bu | H |  | 121–123 |
| 109 | CF₃ | H | Cl | H | Et | H | 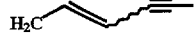 | 164–166 |
| 110 | CF₃ | H | Cl | H | c-Pr | H | 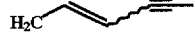 | 233–235 |
| 111 | CF₃ | H | Cl | H | i-Pr | H |  | 222–224 |
| 112 | Cl | H | H | H | Et | H | 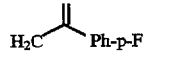 | 238–239 |
| 113 | CF₃ | H | Cl | H | Et | H | H₂C≡≡—OMe | 141–143 |
| 114 | CF₃ | H | Cl | H | Me | H |  | 147–149 |

TABLE 1-continued
4-Amino-2-quinolinone derivatives
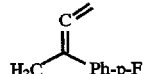
(I)
| No. | R₁ | R₂ | R₃ | R₄ | R₅ | R₆ | R₇ | m.p. (°C.) |
|---|---|---|---|---|---|---|---|---|
| 115 | CF₃ | H | Cl | H | i-Pr | H | 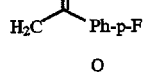 | 100–102 |
| 116 | CF₃ | H | Cl | H | i-Pr | H | 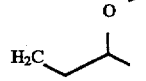 | 144–145 |
| 117 | CF₃ | H | Cl | H | Me | H | 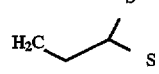 | 167–168 |
| 118 | CF₃ | H | Cl | H | Me | H | 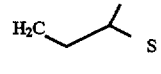 | 107–110 |
| 119 | CF₃ | H | Cl | H | Et | H | 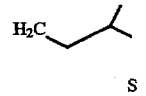 | 103–105 |
| 120 | CF₃ | H | Cl | H | c-Pr | H | 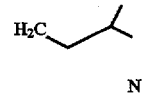 | 135–137 |
| 121 | CF₃ | H | Cl | H | i-Bu | H | 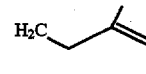 | 92–94 |
| 122 | H | H | F | H | Me | H | 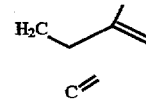 | 307–309 |
| 123 | CF₃ | H | Cl | H | Et | H | 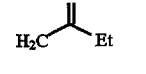 | 243–244 |
| 124 | CF₃ | H | Cl | H | c-Pr | H | 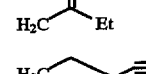 | 152–153 |
| 125 | CF₃ | H | Cl | H | Me | H | 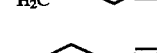 | 135–136 |
| 126 | CF₃ | H | Cl | H | Me | H |  | 109–111 |
| 127 | CF₃ | H | Cl | H | Et | H | 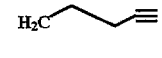 | 117–118 |
| 128 | CF₃ | H | Cl | H | c-Pr | H | 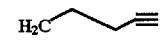 | 139–141 |
| 129 | CF₃ | H | Cl | H | i-Bu | H | H₂C–C≡CH | 94–95 |

TABLE 1-continued

4-Amino-2-quinolinone derivatives (I)

| No. | R$_1$ | R$_2$ | R$_3$ | R$_4$ | R$_5$ | R$_6$ | R$_7$ | m.p. (°C.) |
|---|---|---|---|---|---|---|---|---|
| 130 | CF$_3$ | H | Cl | H | Me | H | H$_2$C-CH=CH-N-N= | 232–234 |
| 131 | CF$_3$ | H | Cl | H | i-Bu | H | H$_2$C-CH=CH-N-N= | 179–181 |

Preparation of the present compounds of formula (I) is illustrated further in the following examples.

EXAMPLE 1

6-Chloro-3-cyclopropanecarbonyl-4-(2,2-dimethoxyethylamino)-8-trifluoromethyl-2-quinolinone (9)

6-Chloro-3-cyclopropanecarbonyl-4-methylsulfoxy-8-trifluormethyl-2-quinolinone (377 mg, 1 mmol) and 2,2-dimethoxyethylamine (105 mg, 1 mmol) were dissolved in tetrahydrofurane (20 ml) and stirred for 24 hr at room temperature. After completion of reaction, solvent was removed under reduced pressure and residue was recrystallized from ethanol to give desired product (335 mg, yield: 80%).

$^1$H-NMR (CDCl$_3$): δ0.7–1.2(m,4H), 3.4(s, 6H), 3.6–3.8 (m,1H), 4.4(t, 1H), 4.5–4.9(m, 2H), 7.7(d, 1H), 8.8 (d, 1H), 9.5(br, 1H), 11.6(br, 1H).

EXAMPLE 2

6-Chloro-4-(2,2-dimethoxyethylamino)-3-isobutyryl-8-trifluoromethyl-2-quinolinone (10)

6-Chloro-3-isobutyryl-4-methylsulfoxy-8-trifluoromethyl-2-quinolinone (379 mg, 1 mmol) and 2,2-dimethoxyethylamine (105 mg, 1 mmol) were used and the reaction was carried out as in the above process of example 1 to obtain the desired product (307 mg, yield: 73%).

$^1$H NMR (CDCl$_3$): δ 1.5(d, 6H), 3.6–3.8(m, 1H), 3.8(s, 6H), 4.4(t, 1H), 4.5–4.9(m, 2H), 8.1(d, 1H), 8.8(d, 1H), 9.9(br, 1H), 12.2(br, 1H).

EXAMPLE 3

3-Acetyl-6-chloro-4-(N-methyl-N'-propargylamino)-8-trifluoromethyl-2-quinolinone (12)

3-Acetyl-6-chloro-4-methylsulfoxy-8-trifluoromethyl-2-quinolinone (351 mg, 1 mmol) and N-methyl-N'-propargylamine (69 mg, 1 mmol) were used and the reaction was carried out as in the above process of example 1 to obtain the desired product (235 mg, yield: 66%).

$^1$H NMR (CDCl$_3$): δ2.6(t, 1H), 3.0(s, 3H), 3.4(s, 3H), 4.6 (d, 2H), 8.2 (d, 1H), 8.6 (d, 1H), 14.0 (br, 1H).

EXAMPLE 4

3-Acetyl-4-(N-methyl-N'-propargylamino)-8-trifluoromethyl-2-quinolinone (15)

3-Acetyl-4-methylsulfoxy-8-trifluoromethyl-2-quinolinone (317 mg, 1 mmol) and N-methyl-N'-propargylamine (69 mg, 1 mmol) were used and the reaction was carried out as in the above process of example 1 to obtain the desired product (210 mg, yield: 65%).

$^1$H NMR (CDCl$_3$): δ 2.5 (t, 1H), 2.9 (s, 3H), 3.3(s, 3H), 4.5(d, 2H), 7.4(t, 1H), 8.2(d, 1H), 8.5(d, 1H), 9.6(br, 1H).

EXAMPLE 5

6-Chloro-3-cyclopropanecarbonyl-4-propargylamino-8-trifluormethyl-2-quinolinone (21)

6-Chloro-3-cyclopropanecarbonyl-4-methylsulfoxy-8-trifluormethyl-2-quinolinone (377 mg, 1 mmol) and propargylamine (55 mg, 1 mmol) were used and the reaction was carried out as in the above process of example 1 to obtain the desired product (265 mg, yield: 72%).

$^1$H NMR (CDCl$_3$): δ 1.3–1.6(m, 4H), 2.9(t, 1H), 3.9–4.3 (m, 1H), 4.6(q, 2H), 8.2(d, 1H), 8.8(d, 2H), 12.4(br, 1H).

EXAMPLE 6

3-Acetyl-6-chloro-4-propargylamino-8-trifluoromethyl-2-quinolinone (24)

3-Acetyl-6-chloro-4-methylsulfoxy-8-trifluoromethyl-2-quinolinone (351 mg, 1 mmol) and propargylamine (55 mg, 1 mmol) were used and the reaction was carried out as in the above process of example 1 to obtain the desired product (284 mg, yield: 83%).

$^1$H NMR (CDCl$_3$): δ 2.9(t, 1H), 3.0(s, 3H), 4.5(q, 2H), 8.0(d, 1H), 8.8(d, 2H), 12.3(br, 1H).

EXAMPLE 7

6-Chloro-4-(3,3-diethoxypropylamino)-3-isobutyryl-8-trifluoromethyl-2-quinolinone (31)

6-Chloro-3-isobutyryl-4-methylsulfoxy-8-trifluoromethyl-2-quinolinone (379 mg, 1 mmol) and 3,3- diethoxypropylamine (147 mg, 1 mmol) were used and the reaction was carried out as in the above process of example 1 to obtain the desired product (335 mg, yield: 78%).

$^1$H NMR (CDCl$_3$): δ 0.7–1.5(m, 12H), 2.0–2.4(m, 2H), 3.2–4.0 (m, 6H), 4.2 (m, 1H), 4.7 (t, 1H), 7.8(d, 1H), 8.0(br, 1H), 11.9(br, 1H).

EXAMPLE 8

6-Chloro-3-isoburyryl-4-(3-oxopropylamino)-8-trifluoromethyl-2-quinolinone (32)

6-Chloro-4-(3,3-diethoxypropylamino)-3-isobutyryl-8-trifluoromethyl-2-quinolinone (31) was dissolved in 80% aqueous acetic acid (20 ml) and stirred for 2 h at 70° C. After cooling to room temperature, water (20 ml) was added and the mixture was extracted with ethyl acetate (30 ml). Organic layer was dried (MgSO$_4$), filtered, evaporated and purified by silicagel chromatograph (n-Hexane and Ethyl acetate) to give desired product (280 mg, yield: 72%).

$^1$H NMR (CDCl$_3$): δ 1.3(d, 6H), 3.1(t, 2H), 3.7(q, 2H), 4.2(m, 1H), 7.8(d, 1H), 8.5(d, 1H), 9.1(br, 1H), 10.0(s, 1H), 11.2(br, 1H).

EXAMPLE 9

3-Acetyl-6-chloro-8-trifluoromethyl-4-(3-trimethylsilyl-propargyl-amino)-2-quinolinone (42)

3-Acetyl-6-chloro-4-methylsulfoxy-8-trifluoromethyl-2-quinolinone (351 mg, 1 mmol), 3-trimethylsilylpropargylamine hydrochloride (164 mg, 1 mmol) and excess triethylamine in tetrahydrofurane (20 ml) were stirred for 24 h at room temperature. After evaporating the solvent, 20 ml of methylene chloride was added and the mixture was washed with water (20 ml). Drying (MgSO$_4$) and removing the solvent under reduced pressure gave crude product. Recrystallization in ethanol gave pure product (330 mg, yield: 80%).

$^1$H NMR (CDCl$_3$): δ 0.2(s, 9H), 2.7(s,3H), 4.3(d,2H), 7.8(d, 1H), 8.5(br, 1H), 8.6(d, 1H), 12.0(br, 1H).

EXAMPLE 10

6-Chloro-4-propargylamino-3-propionyl-8-trifluoromethyl-2-quinolinone (44)

6-Chloro-4-methylsulfoxy-3-propionyl-8-trifluoromethyl-2-quinolinone (365 mg, 1 mmol) and propargylamine (55 mg, 1 mmol) were used and the reaction was carried out as in the above process of example 1 to obtain the desired product (310 mg, yield: 87%).

$^1$H NMR (CDCl$_3$): δ 1.2(t, 3H), 2.7(t, 1H), 3.4(q, 2H), 4.3(d, 2H), 7.9(d, 1H), 8.6(br, 1H), 8.7(d, 1H), 12.2(br, 1H).

EXAMPLE 11

3-Acetyl-6-chloro-4-(1,1-dimethylpropargylamino)-8-trifluoromethyl-2-quinolinone (51)

3-Acetyl-6-chloro-4-methylsulfoxy-8-trifluoromethyl-2-quinolinone (351 mg, 1 mmol) and 1,1-dimethytpropargylamine (83 mg, 1 mmol) were used and the reaction was carried out as in the above process of example 1 to obtain the desired product (322 mg, yield: 87%).

$^1$H NMR (CDCl$_3$): δ 1.5(s, 6H), 2.5(t, 1H), 2.6(s, 3H), 7.7(m, 1H), 8.4(m, 1H), 9.1(br, 1H), 12.0(br, 1H).

EXAMPLE 12

3-Acetyl-6-chloro-4-(3-phenylallylamino)-8-trifluoromethyl-2-quinolindne (62)

3-Acetyl-6-chloro-4-methylsulfoxy-8-trifluoromethyl-2-quinolinone (351 mg, 1 mmol) and 3-phenylallylamine (83 mg, 1 mmol) were used and the reaction was carried out as in the above process of example 1 to obtain the desired product (286 mg, yield: 68%).

$^1$H NMR (CDCl$_3$): δ 2.8(s,3H), 4.3(t, 2H), 6.0–6.7(m, 2H), 7.4(s, 5H), 7.7(d, 1H), 8.1 (br, 1H), 8.5(d, 1H), 12.1(br, 1H).

EXAMPLE 13

6-Chloro-4-(2-chloroallylamino)-3-propionyl-8-trifluoromethyl-2-quinolinone (76)

6-Chloro-4-methylsulfoxy-3-propionyl-8-trifluoromethyl-2-quinolinone (365 mg, 1 mmol) and 2-chloroallylamine (92 mg, 1 mmol) were used and the reaction was carried out as in the above process of example 1 to obtain the desired product (279 mg, yield: 71%).

$^1$H NMR (CDCl$_3$): δ 1.2(t, 3H), 3.3(q, 2H), 4.2(d, 2H), 5.6(s, 2H), 7.8(d, 1H), 8.0(br, 1H), 8.5(d, 1H), 12.3(br, 1H).

EXAMPLE 14

6-Chloro-4-(N,N'-dipropargylamino)-3-isobutyryl-8-trifluommethyl-2-quinolinone (93)

6-Chloro-3-isobutyryl-4-methylsulfoxy-8-trifluoromethyl-2-quinolinone (379 mg, 1 mmol) and N,N'-dipropargylamine (93 ml, 1 mmol) were used and the reaction was carried out as in the above process of example 1 to obtain the desired product (290 mg, yield: 71%).

$^1$H NMR (CDCl$_3$): δ 1.2(d, 6H), 2.3(t, 2H), 4.0–4.3(m, 1H), 4.3(d, 4H), 8.0(d, 1H), 8.3(d, 1H), 13.1(br, 1H).

EXAMPLE 15

3-Acetyl-6-chloro-4-(3-phenylpropargylamino)-8-trifluoromethyl-2-quinolinone (99)

3-Acetyl-6-chloro-4-methylsulfoxy-8-trifluoromethyl-2-quinolinone (351 mg, 1 mmol) and 3-phenylpropargylamine hydrochloride (167 mg, 1 mmol) were used and the reaction was carried out as in the above process of example 10 to obtain the desired product (305 mg, yield: 73%).

$^1$H NMR (CDCl$_3$): δ 2.7(s, 3H), 4.5(d, 2H), 7.5(s, 5H), 7.8(d, 1H), 8.6(d, 2H), 12.0(br, 1H).

EXAMPLE 16

3-Acetyl-6-chloro-4-methylthioethylamino-8-trifluoromethyl-2-quinolinone (102)

3-Acetyl-6-chloro-4-methylsulfoxy-8-trifluoromethyl-2-quinolinone (351 mg, 1 mmol) and methylthioethylamine (91 mg, 1 mmol) were used and the reaction was carried out as in the above process of example 1 to obtain the desired product (287 mg, yield: 76%).

$^1$H NMR (CDCl$_3$): δ 2.15(s, 3H), 2.7(s, 3H), 2.8(t, 2H), 3.6(q, 2H), 7.7(br, 1H), 8.1(br, 1H), 8.5(br, 1H), 12.0(br, 1H).

EXAMPLE 17

3-Acetyl-6-chloro-4-[2-(4-fluorophenyl)-2,3-butadienylamino]-8-trifluoromethyl-2-quinolinone (114)

3-Acetyl-6-chloro-4-methylsulfoxy-8-trifluoromethyl-2-quinolinone (351 mg, 1 mmol) and methylthioethylamine (91 mg, 1 mmol) were used and the reaction was carried out as in the above process of example 1 to obtain the desired product (369 mg, yield: 82%).

¹H NMR (CDCl₃): δ 2.6(s, 3H), 3.6(t,2H), 5.2(t, 2H), 7.2(m, 4H), 7.8(d, 1H), 8.5(br, 1H), 8.6(d, 1H), 11.8(br, 1H).

The compounds of formula (I) according to the present invention have highly curative and protective fungicidal activity for plant phathogens as follows; for example, rice blast (*Piricularia oryzae*), rice sheath blight (*Rhizoctonia solani*), cucumber gray mold (*Botrytis cinerea*), cucumber powdery mildew (*Sphaerotheca fuliginea*), cucumber downy mildew (*Pseudoperonospora cubensis*), grape downy mildew (*Plasmopora viticola*), tomato late blight (*Phytophthora infestans*), rice brown spot (*Cochliobolus miyabeanus*), peanut brown leaf spot (*Cercospora arachidicola*), barley powdery mildew (*Erysiphe graminis*), wheat leaf rust (*Puccinia recondita*), wheat stem rust (*Puccinis graminis*), and wheat eye spot (*Pseudocercosporella herpotrichoides*). Especially, the compounds of present invention showed strong fungicidal activity against rice blast and wheat leaf rust.

The fungicidal activities of 4-amino-2-quinolinone derivatives of formula (I) according to the present invention prepared by the above examples were tested as follow; wherein all the test chemicals were readily dispersed in a standard formulation of acetone in water and a surfactant. Ten ml of acetone containing 10 mg of the chemical was diluted in 90 ml of Tween-20 solution producing 100 ppm solution of chemicals of above examples. Fifty ml of this chemical solution was sprayed to plants on the turntable at the same time. Two pots of plants were duplicately tested for fungicidal activity against 6 plant diseases, respectively.

TEST 1

Fungicidal test for rice blast (RCB)

Evaluation of activity against blast was done with rice plants in the second leaf stage, grown in 5 cm pots with a foliage spray. Fifty ml test material was sprayed on the foliage. After the spray deposit had dried, the plants were inoculated with a suspension of conidia in water (1×10⁶ spores/ml) and placed in a dew chamber at 25° C. for 24 hrs. For inocuhm preparation, rice blast fungus was incubated on rice polish agar medium at 26° C. for 2 weeks, and then scratched airial roycelia with rubber and irradiated with near UV light for 2 days. The plants were then held in lighted growth chamber (26±2° C., 85%) for an additional 5 days, and rated on the disease severity.

TEST 2

Fungicidal test for rice sheath blast (RSB)

Rice plants in the third leaf stage were sprayed with 50 ml of chemical solution on the turntable. One day after drying, treated plants were inoculated by injecting inoculum, incubated in wheat bran medium at 25° C. for 7 days, macerated into the mixer at the base of the rice plants. The pots were moved to a lighted dew chamber at 28° C. and then held for 5 days. The disease severity of each pot was examined and compared with the standard rating diagram.

TEST 3

Fungicidal test for cucumber gray mold (CGM)

Cucumber plants grown in the first leaf stage were sprayed with 50 ml of chemical solution while pots were rotated on the truntable. After the spray deposit had dried for one day, the treated foliage of cucumber was inoculated with conidia (1×10⁶ spores/ml of *B. cinerea*), incubated on potato dextrose agar medium at 25° C. for 15 days by leaf spray to all four sides of plants until just before runoff and then placed in 20° C. dew chamber for 4–5 days. The disease rating was made by examining the treated plants and comparing the percent disease on a leaf with the standard rating diagram.

TEST 4

Fungicidal test for tomato late blight (TLB)

Tests were carried out onto tomato plants grown in 5 cm polyvinyl pots for 14 days by leaf spray. The foliage was sprayed to run off with the test chemical while the plant rotated on a turntable. After the spray deposit dried for one day, the treated plants were inoculated by spraying them with a suspension of zoosporangia (1×10⁵ zoosporangia/ml) incubated on V-8 juice agar medium at 20° C. for 2 weeks and then placed in a dew chamber at 18° C. for 48 hrs. The disease severity was rated after 4 days of inoculation.

TEST 5

Fungicidal test for wheat leaf rust (WLR)

Tests were carried out on wheats (cultivar; Chokwang) grown in polyvinyl pots (diameter; 5 cm) for 7 days by foliage spray. The first leaf was sprayed while plants were rotating on a turntable with 50 ml of a chemical solution. After the spray deposit dried, plants were dusted with a uredospores colonled on the second leaf of wheat and placed in a moist chamber at 20° C. for 24 hours. One day after inoculation, plant were moved to the plant growth chamber (20° C., 70% RH) for inducing the disease. The fungicidal effect of the applied chemicals was investigated by observing the share of diseased area after ten days.

TEST 6

Fungicidal test for barley powdery mildew (BPM)

The barley powdery mildew is an obligately parasitic fungus that must be transferred directly from infected plants to healthy plants in a relatively dry environment. The host plants (cultivar; Allbori) sowed in polyvinyl pot (diameter; 5 cm) were grown in a greenhouse for 7 days. Healthy young barley with fully expanded primary leaf was sprayed with a suspension of a test material. One day after drying, the applied plants were dusted with conidia of *Erysiphe graminis* formed on the primary leaf of barley. The inoculated plants were placed in a plant growth chamber at 22°–24° C. and then induced with the powdery mildew. The disease severity was rated after 7 days of inoculation.

Fungicidal activity of test chemicals against the above 6 plant diseases is shown in Table 2 calculated by formula below.

Control value(%) = 1 − $\left( \frac{\text{Percent of disease area in treatment group}}{\text{Percent of disease area in untreated control group}} \right) \times 100$

TABLE 2

Fungicidal activity of the 4-amino-2-quinolinone of formula (I)

| Comp. No. | RCB | RSB | CGM | TLB | WLR | BPM |
|---|---|---|---|---|---|---|
| 2 | 96 | 25 | 50 | 34 | 99 | 63 |
| 7 | 21 | 40 | 0 | 26 | 98 | 58 |
| 8 | 86 | 45 | 50 | 30 | 95 | 26 |
| 12 | 99 | 65 | 0 | 10 | 100 | 95 |
| 13 | 100 | 5 | 8 | 0 | 98 | 76 |
| 14 | 100 | 0 | 25 | 0 | 99 | 71 |
| 16 | 94 | 40 | 60 | 0 | 100 | 100 |
| 17 | 99 | 20 | 44 | 20 | 99 | 92 |
| 21 | 97 | 60 | 0 | 0 | 99 | 0 |
| 22 | 90 | 85 | 44 | 20 | 99 | 0 |
| 24 | 99 | 45 | 0 | 29 | 99 | 0 |
| 28 | 99 | 20 | 0 | 32 | 100 | 73 |
| 29 | 99 | 100 | 0 | 0 | 100 | 0 |

TABLE 2-continued

Fungicidal activity of the 4-amino-2-quinolinone of formula (I)

| Comp. No. | RCB | RSB | CGM | TLB | WLR | BPM |
|---|---|---|---|---|---|---|
| 30 | 88 | 53 | 0 | 20 | 95 | 0 |
| 31 | 91 | 5 | 44 | 25 | 100 | 60 |
| 32 | 25 | 11 | 19 | 53 | 100 | 10 |
| 33 | 50 | 95 | 38 | 0 | 100 | 25 |
| 35 | 99 | 35 | 8 | 13 | 98 | 0 |
| 38 | 0 | 53 | 0 | 8 | 100 | 76 |
| 44 | 100 | 82 | 15 | 46 | 100 | 0 |
| 45 | 99 | 18 | 0 | 53 | 95 | 0 |
| 46 | 100 | 65 | 0 | 49 | 100 | 71 |
| 53 | 99 | 20 | 0 | 69 | 98 | 14 |
| 54 | 0 | 67 | 0 | 56 | 99 | 25 |
| 57 | 99 | 60 | 0 | 79 | 95 | 9 |
| 59 | 96 | 47 | 0 | 83 | 98 | 30 |
| 64 | 99 | 40 | 0 | 87 | 100 | 0 |
| 65 | 57 | 0 | 0 | 72 | 95 | 30 |
| 67 | 99 | 47 | 0 | 95 | 100 | 0 |
| 68 | 89 | 0 | 0 | 36 | 100 | 30 |
| 70 | 99 | 0 | 15 | 52 | 53 | 0 |
| 72 | 99 | 78 | 0 | 13 | 98 | 0 |
| 74 | 99 | 0 | 28 | 78 | 96 | 9 |
| 75 | 99 | 94 | 46 | 74 | 99 | 55 |
| 76 | 100 | 56 | 34 | 74 | 99 | 0 |
| 77 | 99 | 44 | 28 | 83 | 100 | 0 |
| 78 | 99 | 78 | 4 | 33 | 99 | 9 |
| 85 | 100 | 6 | 0 | 83 | 99 | 77 |
| 86 | 99 | 17 | 0 | 74 | 99 | 38 |
| 87 | 99 | 40 | 0 | 55 | 99 | 0 |
| 92 | 99 | 25 | 20 | 21 | 100 | 31 |
| 93 | 95 | 0 | 15 | 7 | 99 | 88 |
| 94 | 100 | 50 | 8 | 29 | 93 | 88 |

As shown in the Table 2, the compounds of present invention of formula (I) have broad and high fungicidal activity against tested plant diseases, especially, rice blast and wheat leaf rust.

Also, the compounds according to the present invention have high insecticidal and miticidal activity against noxious insects, for example, house fly, mosquito, cockroach and agricultral insects, for example, Hemiptera such as small brown plant hopper (*Laodephax striatellus* Fallen), brown plant hopper (*Nilaparvata lugens* Stail), white-backed rice plant hopper (*Sogatella furcifera* Horvath), green rice leaf hopper (*Nephotettix cincticeps* Uhler), greenhouse whitefly (*Trialeurodes vaporariorum* Westwood), and green peach aphid (*Myzus persicae* Sulzer); Lepidoptera such as apple leafminer (*Phyllonorycter ringoniella* Matsumura), diamond-back moth (*Plutella xylostella* Curtis), rice armyworm (*Pseuclaletia separata* Walker), cabbage to armyworm (*Mamestra brassicae* Linnaeus), tobacco cutworm (*Spodoptera litura* Fablicius), and common cabbage worm (*Pieris rapae* Linnaeus); Coleoptera such as rice lead beetle (*Oulema oryzae* Kuiwayama), and rice-plant weevil rice curculio (*Echinocnemus squameus* Billbery).

The insecticidal activity of the compounds of the formula (I) according to the present invention was tested by Tests 7~10 as shown below.

The Primary Screening (PRI) was designed to detect initial pest control activity of experimental compounds. The types of activity assayed were acute toxicity and growth disruption. The bioassays were designed to detect contact and ingestion activity.

The stages rested were as follows: adult brown planthopper (BPH), green peach aphid (GPA), and two-spotted spider mire (TSSM), and 3rd instar diamond-back moth (DBM). All experimental compounds were formulated in 5 ml of acetone containing 25 mg of 4-amino-2-quinolinone derivatives of formular (I) and diluted with 45 ml Triton X-100 (100 ppm) solution producing 500 ppm solution of chemicals of present invention.

Formulated compounds were applied to the test species with the individual application methods, respectively.

TEST 7

Insecticidal test for brown plant hopper (BPH)

Root parts of six rice seedlings (cultivar: Dongjin; 5–6 cm in length; 5–10 day old) were rolled with cotton wool pads and rice seedlings were put into the glass test tubes ($\Phi$ 3×15 cm) containing 2 ml water. Three to five day-old adult BPH (20 individuals) were collected from rearing cages by an aspirator, and placed into test tubes.

Test chemicals were dissolved in 5 ml acetone (100%), formulated to the proper concentration in Triton X-100 (100 ppm), and then sprayed onto the BPH directly. The test tubes were covered with nylon cloth and held in an incubator at 25° C. Insect mortalities were recorded at 24 and 48 hours after treatment.

TEST 8

Insecticidal test for green peach aphid (GPA)

Excised tobacco leaf disks (5.5 cm in diameter) were dipped into the prepaxed test chemical solutions (30 sec) and taken out. After drying (30 min), leaf disks were placed in the petridishes ($\Phi$ 5.5×2 cm) and apterous female adult GPAs (20 individuals) were introduced. All petridishes were covered and held in an incubator at 25° C. Insect mortalities were recorded at 24 and 48 hours after treatment.

TEST 9

Insecticidal test for two-spotted spider mite (TSSM)

Excised kidney bean leaf disks (2.5 cm in diameter) were placed on water saturated cotton wool pads fitted into petridishes ($\Phi$5.5×2 cm). Female adult TSSMs (30 individuals) were placed on leaf disks and prepared test chemicals were sprayed. The petridishes were covered and held in an incubator at 25° C. Mite mortalities were recorded at 24 and 48 hours after treatment.

TEST 10

Insecticidal test for diamond-back moth (DBM)

Test chemicals were dissolved in 5ml acetone (100%) and formulated to the proper concentration in Triton X-100 (100 ppm). Excised cabbage leaf disks (5 cm in diameter) were dipped into the solution (30 sec) and taken out. After drying (30 min.), leaf disks were placed in the petridishes ($\Phi$ 5×1 cm) and 3rd instar DBM larvae (10 individuals) were introduced. All petridishes were covered and held in an incubator at 25° C. Insect mortalities were recorded at 24 and 48 hours after treatment.

The mortality (%) of test chemical against the above insects was calculated by the below formula to list the result as the following Table 3.

$$\text{Mortality}(\%) = \frac{\text{No. of dead insects}}{\text{No. of treated insects}} \times 100$$

TABLE 3

Insecticidal effects for 4-amino-2-quinolinone of the formula (I)

| Comp. No. | BPH | GPA | DBM | TSSM |
|---|---|---|---|---|
| 2 | 0 | 0 | 0 | 100 |
| 10 | 10 | 0 | 100 | 0 |
| 12 | 0 | 0 | 90 | 100 |

TABLE 3-continued

Insecticidal effects for 4-amino-2-quinolinone of the formula (I)

| Comp. No. | BPH | GPA | DBM | TSSM |
|---|---|---|---|---|
| 13 | 0 | 0 | 100 | 100 |
| 16 | 0 | 0 | 80 | 100 |
| 21 | 0 | 0 | 100 | 0 |
| 22 | 0 | 0 | 100 | 0 |
| 24 | 0 | 0 | 100 | 0 |
| 28 | 0 | 0 | 100 | 0 |
| 30 | 0 | 0 | 100 | 0 |
| 35 | 0 | 0 | 100 | 0 |
| 37 | 0 | 0 | 100 | 0 |
| 38 | 0 | 0 | 100 | 73 |
| 39 | 0 | 0 | 100 | 0 |
| 41 | 0 | 0 | 100 | 0 |
| 44 | 0 | 0 | 100 | 0 |
| 46 | 0 | 0 | 100 | 0 |
| 49 | 0 | 0 | 100 | 0 |
| 54 | 0 | 0 | 100 | 0 |
| 55 | 20 | 10 | 100 | 0 |
| 57 | 0 | 0 | 100 | 0 |
| 68 | 0 | 0 | 100 | 20 |
| 73 | 0 | 0 | 100 | 0 |
| 74 | 0 | 0 | 100 | 0 |
| 76 | 0 | 0 | 100 | 0 |
| 77 | 0 | 0 | 100 | 0 |
| 78 | 0 | 0 | 100 | 70 |
| 83 | 0 | 0 | 100 | 0 |
| 85 | 0 | 0 | 100 | 100 |
| 86 | 0 | 0 | 100 | 73 |

As shown in Table 3, the compounds of the present invention of formula (I) have good insecticidal activity against diamond back moth (DBM) and miticidal activity against two-spotted spider mite (TSSM).

The compounds of formula (I) of present invention have good pre- and post-emergent herbicidal activity against upland and paddy weeds.

The herbicidal activity test was conducted according to the following methods.

(1) Screening for herbicidal activity in upland condition.

The sterilized sandy loam soil was mixed with a combined fertilizer and filled in test pots having a surface area of 348 cm². After seeding, the pots were covered with the soil finely sieved and kept in a greenhouse at 25° C. mean temperature.

Fourteen mg of each compound weighed for 4 kg/ha and was dissolved in 7 ml of acetone containing surfactant Tween-20, and diluted with the same amount of water. The solution on soil or foliage applied was in a spray volume of 14 ml/348 cm².

Test compounds were applied at 1 and 8–12 days after seeding for pre-emergence and post-emergence, respectively.

The pots were kept in the greenhouse for 2 or 3 weeks, and the herbicidal activity was visually observed on the basis of morphological and physicological symptoms by percent scale, in which 0 represents no activity and 100 represents complete control.

(2) Screening for herbicidal activity in flooded paddy condition.

A sandy loam soil mixed with a combined fertilizer and puddled with water to stick mud was filled in test pots having a surface area of 140 cm².

Two plant of rice seeding at 3rd leaf stage and sprouted rice seeds were transplanted and seeded, respectively. The pots are watered 3 cm deep just after planting. For 4 kg/ha application, 5.6 mg of each compound was dissolved in 2 ml of acetone containing 0.2% Tween-20 and diluted with the same amount of water. Four ml of the solution was applied on the water surface of the pot.

The pots were kept in the greenhouse for 2 or 3 weeks at 25° C. mean temperature, and the herbicidal activity was visually observed on the basis of morphological and physicological symptoms by percent scale.

The plant species employed in these tests were selected from the followings:

Test plants for herbicide screening

| Common Name | Abbreviated Name | Scientific Name |
|---|---|---|
| Upland | | |
| Corn | ZEAMX | Zea mays |
| Soybean | GLXMX | Glycine max |
| Cotton | GOSHI | Gossypium hispitum |
| Wheat | TRZAW | Triticum aestivum |
| Rice | ORYSA | Oryza sativa |
| Common sorghum | SORBI | Sorgum bicolor |
| Barnyardgrass | ECHOR | Echinochlor crus-galli |
| Wheatgrass | AGRSM | Agropyron smithii |
| Large crabgrass | DIGSA | Digitaria sanguinalis |
| Fall panicum | PANDI | Pandicum dichotomiflorum |
| Bindweed | CAGHE | Calystegia japonica |
| Cocklebur | XANSI | Xanthium strumarium |
| Velvetleaf | ABUTH | Abutilon avicennae |
| Indian jointvetch | AESIN | Aeschynomene indica |
| Black nightshade | SOLNI | Solanum nigrum |
| Green foxtail | STEVI | Setaria viridis |
| Orchard grass | DACGL | Dactylis glomerta |
| Japanese brome | BROJA | Bromus japonicus |
| Paddy | | |
| Rice | ORYSA | Oryza sativa |
| Barnyardgrass | ECHOR | Echinochlor crus-galli |
| Bulrush | SCPJU | Scirpus juncoides |
| Monochoria | MOOVA | Monochoria vaginalis |
| Dayflower | ANEKE | Aneilema |
| Umbrellaplant | CYPDI | Cyperus diffomis |
| Falsepimpernel | LIDPY | Lindernia pyxidaria |
| Toothcup | ROTIN | Rotala indica |
| Flat-sedge | CYPSE | Cyperus serofinus |
| Arrow head | SAGPY | Sagittaria pygmaea |
| Water chestnut | ELOKU | Elocharis kuroguwai |
| Pondweed | PTMDI | Potamogeton distinctus |
| Arrow head | SAGTR | Sagittaria trifolia |

Herbicidal activity data of the present test chemical of formula (I) against upland and paddy weeds are shown in Table 4.

TABLE 4

Post-emergent herbicidal activity of the 4-amino-2-quinolinone derivatives (1) (rate = 4 kg/ha).

| Compound No. | SORBI | ECHOR | AGRSM | DIGSA | PANDI | SOLNI | AESIN | ABUTH | XANSI | CAGHE |
|---|---|---|---|---|---|---|---|---|---|---|
| 2 | 0 | 0 | 0 | 0 | 0 | 70 | 100 | 0 | 0 | 0 |
| 5 | 0 | 0 | 0 | 0 | 0 | 100 | 100 | 0 | 30 | 0 |

TABLE 4-continued

Post-emergent herbicidal activity of the 4-amino-2-quinolinone derivatives (1)
(rate = 4 kg/ha).

| Compound No. | SORBI | ECHOR | AGRSM | DIGSA | PANDI | SOLNI | AESIN | ABUTH | XANSI | CAGHE |
|---|---|---|---|---|---|---|---|---|---|---|
| 8 | 0 | 0 | 0 | 0 | 0 | 100 | 40 | 0 | 30 | 0 |

TABLE 5

Herbicidal activity of 4-amino-2-quinolinone derivatives (1) to paddy weeds.

| Compound No. | ORYSA (3-leaf) | ORYSA (seed) | ECHOR | SCPJU | MOOVA | CYPSE | SAGPY |
|---|---|---|---|---|---|---|---|
| 1 | 0 | 30 | 40 | 0 | 0 | 100 | 100 |
| 3 | 0 | 60 | 70 | 0 | 0 | 100 | 40 |
| 6 | 0 | 100 | 100 | 20 | 40 | 100 | 0 |
| 7 | 0 | 30 | 100 | 0 | 0 | 0 | 20 |
| 8 | 10 | 30 | 70 | 0 | 0 | 0 | 100 |
| 17 | 0 | 50 | 20 | 0 | 30 | 100 | 40 |
| 18 | 0 | 20 | 30 | 0 | 40 | 100 | 0 |
| 19 | 0 | 40 | 50 | 0 | 40 | 100 | 20 |
| 20 | 0 | 70 | 60 | 0 | 50 | 100 | 100 |
| 21 | 0 | 30 | 100 | 0 | 0 | 100 | 0 |
| 22 | 0 | 100 | 100 | 30 | 100 | 100 | 0 |
| 23 | 0 | 0 | 40 | 0 | 100 | 0 | 0 |
| 24 | 0 | 100 | 50 | 0 | 40 | 100 | 0 |
| 25 | 10 | 0 | 0 | 0 | 100 | 0 | 0 |
| 26 | 0 | 40 | 0 | 0 | 100 | 0 | 50 |
| 28 | 0 | 100 | 100 | 0 | 0 | 100 | 50 |
| 30 | 5 | 10 | 90 | 30 | 60 | 100 | 0 |
| 35 | 30 | 100 | 100 | 50 | 80 | 100 | 0 |
| 38 | 10 | 100 | 100 | 30 | 100 | 100 | 100 |
| 43 | 10 | 10 | 0 | 100 | 10 | 40 | 0 |
| 44 | 0 | 10 | 100 | 50 | 100 | 20 | 0 |
| 46 | 10 | 100 | 70 | 20 | 60 | 100 | 30 |
| 54 | 0 | 100 | 100 | 100 | 100 | 100 | 0 |
| 57 | 0 | 20 | 100 | 30 | 0 | 100 | 100 |
| 67 | 10 | 100 | 100 | 30 | 100 | 100 | 0 |
| 68 | 10 | 100 | 100 | 0 | 100 | 100 | 0 |
| 74 | 10 | 10 | 100 | 0 | 10 | 0 | 0 |
| 85 | 0 | 10 | 100 | 0 | 0 | 0 | 20 |
| 92 | 5 | 10 | 100 | 10 | 30 | 40 | 10 |
| 102 | 0 | 20 | 100 | 0 | 60 | 0 | 0 |

Useful formulations of the compounds of formula (I) can be prepared by mixing the the active ingredients about 0.01~90 by weight % with proper solid or liquid carrier and supporters such as surfactant, diluent, spreader, synergist, adhesive, and dispersant, etc.

The used solid carrier may be chosen from the inorganic powders such as attapulgite clays, the montmorillonite clays, the diatomaceous earths, kaolinite, bentonite, mica, gypsum, calcium carbonate, apitite, synthesized silicone hydroxide hydrate or plant powders.

And as liquid carriers, alcohols such as methanol, ethanol, ethylene glycol; aromatic hydrocarbons such as benzene, xylene, toluene, naphtha; halohydrocarbons such as chloroform, carbon tetrachloride; ethers such as tetrahydrofurane, dioxane; ketones such as acetone, methyl ethyl ketone; esters such as ethyl acetate, butyl acetate, ethylene glycole acetate; amides such as dimethylformamide; nitriles such as acetonitrile; ether alcoholes such as ethylene glycol diethyl ether, or water etc. can be used.

Surfactants can be various cationic, anionic and nontoxic surfactants.

Cationic surfactants include long chain alkylammoniun salts such as cetyltrimethylammonium bromide, etc.

Anionic surfactants include alkali metal, alkaline earth metal and ammonium salts of alkylaryl sulfonic acids such as dodecyl benzenesulfonic acids; alkylsulfonic acids such as laurylsulfonic acids ligninsulfonic acid; arylsulfonic such as naphthylenesulfonic acid; lauryl ether sulfate; fatty alcohol sulfates; fatty acids; salt of sulfated hexadecanols, octadecanols; salts of sulfated fatty alcohol glycol ethers, etc.

Examples of nonionic surfactants include condensation products of fatty alcohols such as oleyl alcohol or cetyl alcohol; phenols; alkylphenols or caster oil with ethylene oxide or propylene oxide; polyoxy ethylene alkylphenylether; poly oxyethylene fatty acid ester, etc.

Polyvinylalcohol, CMC, gum arabic, etc. can be used as adhesive.

The compositions of the compounds of the present invention may be manufactured as formulation such as powder, wettable powder, granules, emulsifiable concentrates, suspensions, solution, fumigant, gas phase, etc., and their formulations can be used on earth, agricultural products, seedling, seeds, etc.

For example, emulsifiable concentrates or solution may be prepared by uniformly dissolving the compound of formula (I) with hydrocarbon, acetone or alcohol and surfactant.

Wettable powders, which may be compacted to form water dispersible granules, may comprise an intimate mixture of the active compound, inert carrier and surfactants.

The combinations including the compounds according to the present invention may be used by mixing with agricultural chemicals such as insecticides, fungicides, herbicides, plant growth regulants, fertilizer, miticides, or other agricultural chemicals.

Especially, since the known fungicides have resistance, the compounds of formula (I) of more than 1 weight % may be used with the known fungicides including following compounds;
1) N-substituted azoles, for example, prochloraz, triademefon, and flusitazol;
2) pyrimidines, such as fenarimol and nuarimol;
3) morpholines, such as fenpropimorph and tridemorph;
4) piperazines, such as triforine;
5) pyridines, such as pyrifenox;
6) dithiocarbamates, such as maneb and mancozeb;
7) phthalimides, such as captafol;
8) isophthalonitriles, such as chlorothalonil;
9) dicarboximides, such as ipmdione;
10) benzimidazoles, such as benomyl and carbendazim;
11) 2-aminopyrimidines, such as ethirimol;
12) carboxamides, such as carboxin; and
13) dinitrophenols, such as dinocap.

The fungicide combinations of the invention contain at least 1%, generally 20~80% by weight of a compound of formula (I).

What is claimed is:

1. A compound of 4-amino-2-quinolinone derivatives of the formula (I):

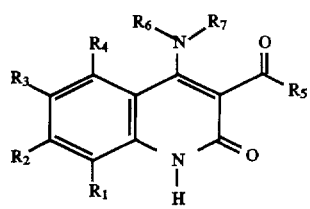

(I)

wherein, $R_1$, $R_2$, $R_3$ and $R_4$ are independently hydrogen, halogen, $C_1$–$C_{10}$ alkyl, $C_1$–$C_3$ haloalkyl, $C_1$–$C_8$ alkoxy, $C_1$–$C_3$ haloalkoxy, $C_1$–$C_3$ alkylthio, $C_1$–$C_3$ haloalkylthio, $NO_2$, CN, $C_1$–$C_4$ alkoxy carbonyl, phenyl, phenoxy, benzoyl, benzenesulfonyl, benzyl or morpholine;

$R_5$ is hydrogen, $C_1$–$C_6$ alkyl, cyclopropyl, phenyl, halophenyl, benzyl or phenylthiomethyl;

$R_6$ is hydrogen, $C_1$–$C_5$ alkyl, $C_3$–$C_6$ alkenyl or $C_3$–$C_6$ alkynyl;

$R_7$ is

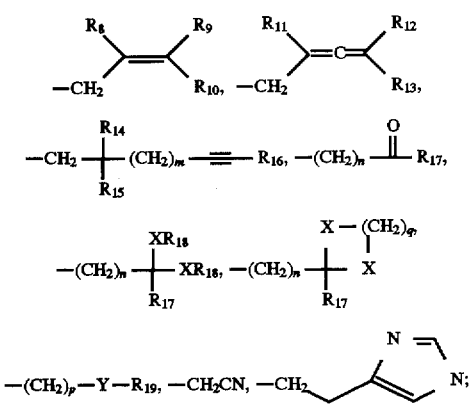

wherein:

$R_8$, $R_9$ and $R_{10}$ are hydrogen, halogen, phenyl or alkynyl, wherein $R_8$, $R_9$ and $R_{10}$ are not hydrogen at same time;

$R_{11}$, $R_{12}$, $R_{13}$, $R_{14}$, $R_{15}$ and $R_{16}$ are hydrogen, halogen, $C_1$–$C_6$ alkyl, alkoxyalkyl, phenyl or $(R_{20})_3$Si;

$R_{17}$ is hydrogen or $C_1$–$C_5$ alkyl;

$R_{18}$ and $R_{19}$ are $C_1$–$C_5$ alkyl;

X is oxygen or sulfur;

Y is sulfur or —S(=O)—;

$R_{20}$ is $C_1$–$C_5$alkyl;

m, n, p and q are 0 to 4; and wherein if $R_{17}$ is hydrogen and n is 0, 1 or 2 then $R_{18}$ is $C_3$–$C_5$ alkyl.

wherein, $R_8$, $R_9$ and $R_{10}$ are independently hydrogen, halogen, phenyl or alkynyl, wherein $R_8$, $R_9$ and $R_{10}$ are not hydrogen at same time;

$R_{11}$, $R_{12}$, $R_{13}$, $R_{14}$, $R_{15}$ and $R_{16}$ are independently hydrogen, halogen, $C_1$–$C_6$ alkyl, alkoxyalkyl, halophenyl, phenyl or $(R_{20})_3$Si;

$R_{17}$ is hydrogen or $C_1$–$C_5$ alkyl;

$R_{18}$ and $R_{19}$ are $C_1$–$C_5$ alkyl;

X is oxygen or sulfur;

Y is sulfur or —S(=O)—;

$R_{20}$ is $C_1$–$C_5$alkyl;

m, n, p and q are 0 to 4; and wherein if $R_{17}$ is hydrogen and n is 0, 1 or 2 then $R_{18}$ is $C_3$–$C_5$ alkyl.

2. The compound of 4-amino-2-quinolinone derivatives or the formula (I) according to claim 1 wherein, $R_1$, $R_2$, $R_3$ and $R_4$ are independently hydrogen, halogen, $C_1$–$C_6$ alkyl, $CF_3$, $NO_2$, CN;

$R_5$ is $C_1$–$C_4$alkyl, cyclopropyl, halophenyl, benzyl;

$R_6$ is hydrogen, $C_1$–$C_5$ alkyl, $C_3$–$C_6$ alkenyl or $C_3$–$C_6$ alkynyl;

$R_7$ is

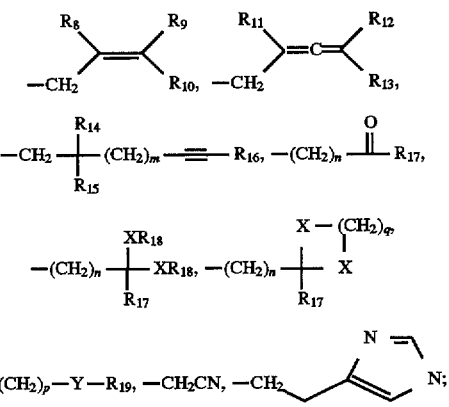

3. A fungicidal composition comprising a fungicidally effective amount of 4-amino-2-quinolinone derivatives of formula (I) as claimed in claim 1.

4. An insecticidal composition comprising a insecticidally effective amount of 4-amino-2-quinolinone derivatives of formula (I) as claimed in claim 1.

5. A herbicidal composition comprising a herbicidally effective amount of 4-amino-2-quinolinone derivatives of formula (I) as claimed in claim 1.

* * * * *

UNITED STATES PATENT AND TRADEMARK OFFICE
CERTIFICATE OF CORRECTION

PATENT NO.: 5,707,931

DATED: January 13, 1998

INVENTOR(S): Chwang Siek Pak; Eun Bok Choi; Gyu Hwan Yon; Heui Cheol Yang; Hyeon Kyu Lee; Ge Hyeong Lee; Jin Pyo Lee; Gyung Ja Choi It is certified that an error appears in the above-identified patent and that said Letters Patent is hereby corrected as shown below:

Claim 1, col. 32, line 12, change "$C_1$-$C_5$alkyl" to --$C_1$-$C_5$ alkyl--;

Claim 2, col. 32, line 21, change "$C_1$-$C_4$alkyl" to --$C_1$-$C_4$ alkyl--;

Claim 2, col. 32, line 50, change "$R_{16}$" to --$R_{18}$--; and

Claim 2, col. 32, line 53, change "$C_1$-$C_5$alkyl" to --$C_1$-$C_5$ alkyl--.

Signed and Sealed this

Thirty-first Day of March, 1998

*Attest:*

BRUCE LEHMAN

*Attesting Officer*     *Commissioner of Patents and Trademarks*